United States Patent [19]

Stern et al.

[11] Patent Number: 5,117,063
[45] Date of Patent: May 26, 1992

[54] METHOD OF PREPARING 4-AMINODIPHENYLAMINE

[75] Inventors: Michael K. Stern; James K. Bashkin, both of University City, Mo.

[73] Assignee: Monsanto Company, St. Louis, Mo.

[21] Appl. No.: 719,876

[22] Filed: Jun. 21, 1991

[51] Int. Cl.⁵ ............... C07C 209/02; C07C 209/26; C07C 209/36; C07C 209/38

[52] U.S. Cl. .................... 564/398; 564/397; 564/408; 564/420; 564/421; 564/423; 564/433; 564/434

[58] Field of Search ............ 564/397, 398, 408, 420, 564/421, 422, 423

[56] References Cited

U.S. PATENT DOCUMENTS

| | | | |
|---|---|---|---|
| 3,847,990 | 11/1974 | Blahak | 260/576 |
| 4,122,118 | 10/1978 | George et al. | 260/576 |
| 4,140,716 | 2/1979 | Maender et al. | 260/562 |
| 4,145,936 | 5/1979 | Sturm | 260/576 |
| 4,178,315 | 12/1979 | Zengel et al. | 260/647 |
| 4,187,248 | 2/1980 | Merten et al. | 260/576 |
| 4,187,249 | 2/1980 | Maender et al. | 260/576 |
| 4,196,146 | 4/1980 | Merten et al. | 260/576 |
| 4,209,463 | 6/1980 | Maender et al. | 260/576 |
| 4,404,401 | 9/1983 | Zengel et al. | 564/416 |
| 4,479,008 | 10/1984 | Batorewicz | 564/433 |
| 4,518,803 | 5/1985 | Batorewicz | 564/410 |
| 4,614,817 | 9/1986 | Maender et al. | 564/406 |
| 4,670,595 | 6/1987 | Podder et al. | 564/406 |
| 4,683,332 | 7/1987 | Sturm | 564/414 |
| 4,760,186 | 7/1988 | Solodar | 564/415 |

FOREIGN PATENT DOCUMENTS 1440767 6/1976 United Kingdom .

OTHER PUBLICATIONS

Ayyangar et al., *Tetrahedron Letters*, vol. 31, No. 22, pp. 3217–3220 (1990).
Wohl, *Chemische Berichte*, 36, p. 4135 (1903).
Wohl, *Chemische Berichte*, 34, p. 2442 (1901).

*Primary Examiner*—Richard L. Raymond
*Attorney, Agent, or Firm*—Charles E. Smith; Paul L. Passley; James C. Bolding

[57] ABSTRACT

A method of producing 4-ADPA is disclosed wherein aniline and nitrobenzene are reacted under suitable conditions to produce 4-nitrodiphenylamine and/or 4-nitrosodiphenylamine and/or their salts, either or both of which are subsequently reduced to produce 4-ADPA. The 4-ADPA can be reductively alkylated to produce p-phenylenediamine products which are useful as antiozonants.

94 Claims, No Drawings

METHOD OF PREPARING 4-AMINODIPHENYLAMINE

BACKGROUND OF THE INVENTION

1. Field of the Invention

The present invention relates to methods for preparing 4-aminodiphenylamine (4-ADPA) and, more particularly, relates to a method for preparing 4-ADPA wherein aniline is reacted with nitrobenzene in the presence of a base, and under conditions wherein the amount of protic material, e.g., water, is controlled, to produce a mixture rich in the salt of 4-nitrodiphenylamine and/or the salt of 4-nitrosodiphenylamine. The 4-nitrodiphenylamine and/or 4-nitrosodiphenylamine salts are isolated and subsequently hydrogenated or, alternatively, the reaction mixture itself is hydrogenated, to produce 4-ADPA in high yield. The present invention also relates to methods for preparing 4-ADPA intermediates as well as to alkylated p-phenylenediamine products useful as antioxidants.

2. Related Art

It is known to prepare 4-ADPA by way of a nucleophilic aromatic substitution mechanism, wherein an aniline derivative replaces halide. This method involves preparation of a 4-ADPA intermediate, namely 4-nitrodiphenylamine (4-NDPA) followed by reduction of the nitro moiety. The 4-NDPA is prepared by reacting p-chloronitrobenzene with an aniline derivative, such as formanilide or an alkali metal salt thereof, in the presence of an acid acceptor or neutralizing agent, such as potassium carbonate, and, optionally, utilizing a catalyst. See, for example, U.S. Pat. Nos. 4,187,248; 4,683,332; 4,155,936; 4,670,595; 4,122,118; 4,614,817; 4,209,463; 4,196,146; 4,187,249; 4,140,716. This method is disadvantageous in that the halide that is displaced is corrosive to the reactors and appears in the waste stream and must therefore be disposed of at considerable expense. Furthermore, use of an aniline derivative such as formanilide, and use of p-chloro-nitrobenzene, requires additional manufacturing equipment and capabilities to produce such starting materials from aniline and nitrobenzene, respectively.

It is also known to prepare 4-ADPA from the head-to-tail coupling of aniline. See, for example, G.B. 1,440,767 and U.S. Pat. No. 4,760,186. This method is disadvantageous in that the yield of 4-ADPA is not acceptable for a commercial process. It is also known to decarboxylate a urethane to produce 4-NDPA. See U.S. Pat. No. 3,847,990. However, such method is not commercially practical in terms of cost and yield.

It is known to prepare 4-ADPA by hydrogenating p-nitrosodiphenylhydroxylamine which can be prepared by catalytic reduction of nitrosobenzene utilizing, as a reducing agent, aliphatic compounds, benzene, naphthalene or ethylenically unsaturated compounds. See, for example, U.S. Pat. Nos. 4,178,315 and 4,404,401. It is also known to prepare p-nitrosodiphenylamine from diphenylamine and an alkyl nitrate in the presence of excess hydrogen chloride. See, for example, U.S. Pat. Nos. 4,518,803 and 4,479,008.

It is also known to produce 4-nitrosodiphenylamine by reacting acetanilide and nitrobenzene in DMSO in the presence of sodium hydroxide and potassium carbonate at 80° C. for 5 hours. See Ayyangar et al., Tetrahedron Letters, Vol. 31, No. 22, pp. 3217-3220 (1990). See also, Wohl, Chemische Berichte, 36, p. 4135 (1903) and Chemische Berichte, 34, p. 2442 (1901). However, the yield of 4-nitrosodiphenylamine is low and is therefore not commercially practical. Furthermore, such method requires utilization of an aniline derivative, namely, acetanilide, and therefore increases the cost of the starting materials.

The process of the present invention does not include a halide source and therefore eliminates the expensive halide removal from the waste stream. In addition, the process of the present invention is much less expensive in terms of manufacturing costs, as well as the cost of raw materials, because instead of the derivatives of aniline and nitrobenzene, the present method utilizes aniline and nitrobenzene directly.

SUMMARY OF THE INVENTION

The present invention is directed to a method of preparing 4-ADPA intermediates, namely 4-nitrodiphenylamine (4-NDPA) and the salts thereof, and/or 4-nitrosodiphenylamine (p-NDPA) and/or the salts thereof, wherein aniline and nitrobenzene are brought into reactive contact in a suitable solvent system, and then reacted in the presence of a base and under conditions wherein the amount of protic material, such as water, is controlled. The resulting reaction mixture is rich in 4-ADPA intermediates, including the 4-nitrodiphenylamine and/or 4-nitrosodiphenylamine salts. The process can be utilized according to the teachings of the present invention to produce a high yield of the 4-nitroso product (p-nitrosodiphenylamine and its salt) with little or no 4-nitro product. The 4-nitroso reaction product mixture can then be hydrogenated directly, or the 4-nitroso product can then be isolated and subsequently hydrogenated, to produce 4-ADPA in high yield. Similarly, the 4-nitro product (4-nitrodiphenylamine and its salt) can be produced in high yield with little or no 4-nitroso product, and the 4-nitro product, or the isolated 4-nitro product, can be hydrogenated to produce 4-ADPA in high yield. Alternatively, the 4-nitro and 4-nitroso products are both produced and are not isolated but the reaction mixture is hydrogenated directly to produce 4-ADPA. The resulting 4-ADPA can be utilized to prepare alkylated products of p-phenylenediamine, which products are useful as antioxidants and antiozonants. Alternatively, the 4-ADPA intermediates can be reduced and the reduced material alkylated in the same reaction vessel utilizing a ketone as a solvent.

DETAILED DESCRIPTION OF THE INVENTION

The subject method for producing 4-ADPA intermediates involves the steps of:

a) bringing aniline and nitrobenzene into reactive contact in a suitable solvent system;

b) reacting the aniline and nitrobenzene in a confined zone, such as a reactor, at a suitable temperature and in the presence of a suitable base and a controlled amount of protic material, such as water, to produce 4-nitrodiphenylamine and its salt and/or 4-nitrosodiphenylamine and its salt.

For producing 4-ADPA, the subject method includes the following step:

c) reducing the 4-nitrosodiphenylamine and its salt and/or the 4-nitrodiphenylamine and its salt to produce 4-ADPA.

For producing alkylated p-phenylenediamines, the subject method includes the step of:

d) reductively alkylating the 4-ADPA of Step c).

As utilized herein, the term "4-ADPA intermediates" means 4-nitrodiphenylamine, 4-nitrosodiphenylamine (also referred to as p-nitrosodiphenylamine) and the salts thereof. Thus, reference to "one or more 4-ADPA intermediates" refers to one or both of the neutral compounds, i.e., those that are not in the form of a salt, and/or the salt of one or both of such compounds. The salt is produced in the reaction mixture from reaction of the 4-nitro and/or 4-nitroso products with the base. Thus, the reaction mixture produced in the method of the present invention can include one of the compounds or salts or any combination thereof depending on the specific reaction conditions selected.

The molar ratio of aniline to nitrobenzene can vary from a large excess of nitrobenzene to a large excess of aniline. Preferably, the reaction is conducted utilizing an excess of aniline. The ratio of 4-nitro to 4-nitroso produced in the reaction of the present invention can be controlled by varying the ratio of aniline to nitrobenzene. The higher the ratio of aniline to nitrobenzene, the higher the ratio of 4-nitroso to 4-nitro. Conversely, the higher the ratio of nitrobenzene to aniline, the higher the ratio of 4-nitro to 4-nitroso.

Azobenzene is also produced in this reaction in variable quantities depending on the reaction conditions. One way of controlling azobenzene production is through the ratio of aniline to nitrobenzene. Thus, as this ratio is increased, the amount of azobenzene generally decreases. As discussed below, and as illustrated in the Examples set forth below, other variables, such as the amount of base and oxygen, can also affect the amount of azobenzene produced. Thus, utilizing the teachings of the present invention, one skilled in the art can conduct the reaction of the present invention to control the amount of azobenzene that is produced.

Suitable solvent systems include, but are not limited to, solvents such as, for example, dimethylsulfoxide, N-methylpyrolidone, dimethylformamide, aniline, pyridine, nitrobenzene and the like, as well as mixtures thereof. Preferably, aniline is used in excess in the reaction as stated above, and the aniline in excess of the molar amount of nitrobenzene serves as the solvent. As described in more detail below, solvent mixtures can be utilized wherein one or more of the suitable solvents and another solvent, such as a controlled amount of a protic solvent, e.g., methanol, are combined.

Suitable bases include, but are not limited to, organic and inorganic bases such as, for example, alkali metals, such as sodium metal, alkali metal hydrides, hydroxides and alkoxides, such as sodium hydride, lithium hydroxide, sodium hydroxide, cesium hydroxide, potassium hydroxide, potassium t-butoxide, and the like, including mixtures thereof. Other acceptable base materials include, but are not limited to, phase transfer catalysts in conjunction with a suitable base source such as tetraalkylammonium hydroxides, e.g., tetramethylammonium hydroxide, and other combinations of phase transfer catalysts and suitable bases such as suitable bases in conjunction with aryl ammonium salts, crown ethers and the like, and amine bases, such as lithium bis(trimethylsilyl) amide, and the like, including mixtures thereof. Preferred materials (bases) for use as bases are tetraalkylammonium hydroxides such as tetramethylammonium hydroxide. Preferably, the base is added to the aniline to produce a mixture which is then combined with the nitrobenzene. Alternatively, the base can be added after the aniline and nitrobenzene have been combined. Addition of materials can be above or below surface addition. The amount of base utilized in the present process can vary over a wide range. For example, the reaction can be conducted in a manner which is limiting in base or the reaction can be conducted in a manner which is limiting in nitrobenzene or aniline depending, among other factors, on the desired degree of minimization of azobenzene.

The reaction is conducted at a suitable temperature which can vary over a wide range. For example, the temperature can fall within a range of from about $-10°$ C. to about 150° C., such as from about 0° C. to about 100° C., preferably from about 10° C. to about 80° C. A most preferred temperature for conducting the reaction of the present invention is from about 40° C. to about 70° C., such as at 50° C. Where aniline is utilized as the solvent under aerobic reaction conditions, as the temperature of the reaction increases, the amount of azobenzene produced increases. However, where the reaction is conducted in aniline under anaerobic conditions, higher temperatures do not necessarily increase the amount of azobenzene. Where production of azobenzene is not a problem, higher temperatures will be suitable. However, where it is desired to minimize the amount of azobenzene, lower temperatures or anaerobic reaction conditions are more suitable. Alternatively, to minimize the amount of azobenzene while conducting the reaction at higher temperatures, a solvent other than aniline can be used and the ratio of aniline to nitrobenzene can be controlled.

Control of the amount of protic material present in the reaction is important. Generally, when the reaction is conducted in aniline, water present in the reaction in an amount greater than about 4% $H_2O$, (based on volume of the reaction mixture) inhibits the reaction of the aniline with the nitrobenzene to an extent where the reaction is no longer significant. Reducing the amount of water to below the 4% level causes the reaction to proceed in an acceptable manner. When tetramethylammonium hydroxide is utilized as a base with aniline as the solvent, as the amount of water is reduced further, e.g., down to about 0.5% based on the volume of the reaction mixture, the total amount of 4-nitrodiphenylamine and 4-nitrosodiphenylamine increases with some loss in selectivity so that more 2-nitrodiphenylamine is produced but still in minor amounts. Thus, the present reaction could be conducted under anhydrous conditions. A "controlled amount" of protic material is an amount up to that which inhibits the reaction of aniline with nitrobenzene, e.g., up to about 4% $H_2O$ based on the volume of the reaction mixture when aniline is utilized as the solvent. The upper limit for the amount of protic material present in the reaction varies with the solvent. For example, when DMSO is utilized as the solvent and tetramethylammonium hydroxide is utilized as the base, the upper limit on the amount of protic material present in the reaction is about 8% $H_2O$ based on the volume of the reaction mixture. When aniline is utilized as a solvent with the same base, the upper limit is 4% $H_2O$ based on the volume of the reaction mixture. In addition, the amount of protic material tolerated will vary with type of base, amount of base, and base cation, used in the various solvent systems. However, it is within the skill of one in the art, utilizing the teachings of the present invention, to determine the specific upper limit of the amount of protic material for a specific solvent, type and amount of base, base cation and the like. The minimum amount of protic material necessary to maintain selectivity of the desired products will also depend on the solvent, type and amount of base, base cation and the like, that is utilized and can also be determined by one skilled in the art.

Since the amount of protic material present in the reaction is important, it is preferred to reduce the amount of protic material present as much as possible and then add back to the reaction the desired amount, e.g., 0.5 vol. % when aniline is used as the solvent. Protic materials that can be utilized to add back to the reaction are known to those skilled in the art and include, but are not limited to, water, methanol and the like. Methods for measuring the amount of protic material and for reducing the amount of protic material as much as possible are well known in the art. For example, the amount of water present in certain reagents can be determined by utilizing a Karl-Fischer apparatus, and the amount of water can be reduced through distillation and/or drying under reduced pressure, drying in the presence of $P_2O_5$ and other agents, azeotropic distillation utilizing, for example, aniline, and the like, including combinations thereof.

The reaction can be conducted under aerobic or anaerobic conditions. Under aerobic conditions, the reaction is conducted essentially as described above in a reaction zone which is exposed to oxygen, usually by exposure to air. Under aerobic conditions, the pressure at which the reaction is conducted can vary and the optimal pressure, as well as the optimal combination of pressure and temperature/pressure conditions, are easily determined by one skilled in the art. For example, the reaction can be conducted at room temperature and at a pressure ranging from about 10 psig to about 250 psig, such as from about 14 to about 150 psig. Under anaerobic conditions, the reaction can be conducted at atmospheric pressure or reduced or increased pressures, in the presence of a neutral gas such as, for example, nitrogen or argon. Optimal conditions for a particular set of reaction parameters, such as temperature, base, solvent and the like, are easily determined by one skilled in the art utilizing the teachings of the present invention. It has been observed that less azobenzene is produced when the reaction is conducted anaerobically with aniline as the solvent. It has also been observed that less azobenzene is produced when the reaction is conducted aerobically with DMSO, and other similar solvents, as the solvent.

The 4-nitrodiphenylamine and/or 4-nitrosodiphenylamine and/or their salts can be reduced to 4-ADPA. The neutral compounds can be generated from the salts utilizing water and/or an acid. See, for example, Example 1D. Alternatively, the salts can be reduced as shown in Example 1A. This reduction can be carried out by any of many known reductive processes, such as using a hydride source, e.g., sodium borohydride in conjunction with palladium- or platinum-on-carbon catalyst. Preferably, this reduction is conducted by a catalytic reduction wherein hydrogenation is effected under hydrogen pressure in the presence of platinum- or palladium-on-carbon, nickel, and the like. This hydrogenation process is described in detail in "Catalytic Hydrogenation in Organic Synthesis", P. N. Rylander, Academic Press, N.Y., p. 299 (1979), which is hereby incorporated herein by reference. Preferably, the hydrogenation is conducted utilizing a platinum-on-carbon catalyst in a suitable solvent such as, for example, either xylene or aniline, mixtures thereof, or mixtures which include water as the solvent and a hydrogen pressure of from 100 psig $H_2$ to about 340 psig $H_2$ at a temperature of about 80° C.

Reductive alkylation of 4-ADPA to produce antiozonants can be conducted by any one of several well known methods. See, for example, U.S. Pat. No. 4,900,868. Preferably, 4-ADPA and a suitable ketone or aldehyde are reacted in the presence of hydrogen and platinum on carbon as catalyst. Suitable ketones include methylisobutyl ketone (MIBK), acetone, methylisoamylketone and 2-octanone. It should be noted that reduction of the 4-ADPA intermediates and alkylation of the reduced material can be conducted in the same reaction vessel utilizing the ketone as a solvent. See, for example, U.S. Pat. No. 4,463,191, and Banerjee et al, J. Chem. Soc. Chem. Comm. 18, 1275–76 (1988).

Contemplated equivalents of the reactants and reagents set forth above are reactants and reagents otherwise corresponding thereto and having the same general properties wherein one or more of the various groups, e.g., $NO_2$, are simple variations. In addition, where a substituent is designated as, or can be, a hydrogen, the exact chemical nature of a substituent which is other than hydrogen at that position is not critical so long as it does not adversely affect the overall activity and/or synthesis procedure.

The chemical reactions described above are generally disclosed in terms of their broadest application to the method of this invention. Occasionally, the reaction conditions may not be applicable as specifically described to each reactant and reagent within the disclosed scope. For example, certain suitable bases may not be as soluble in one solvent as they are in other solvents. The reactants and reagents for which this occurs will be readily recognized by those skilled in the art. In all such cases, either the reactions can be successfully performed by conventional modifications known to those skilled in the art, e.g., by appropriate adjustments in temperature, pressure and the like, by changing to alternative conventional reagents such as other solvents or other bases, by routine modification of reaction conditions, and the like, or other reactions disclosed herein or otherwise conventional, will be applicable to the method of this invention. In all preparative methods, all starting materials are known or are readily preparable from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

All reagents were used as received except that the bases and solvents were dried as described hereinafter. Unless indicated otherwise, all yields were determined by HPLC according to the following method.

Materials and Methods

Aniline and nitrobenzene were reagent grade and were used without further purification. Solvents were purchased from Aldrich Chemical and were anhydrous grade. The tetramethylammonium hydroxide was purchased as the pentahydrate. The solid was dried in a desiccator over $P_2O_5$ under vacuum for several days before use. Titration of the resulting solid showed the dried material to be the dihydrate.

HPLC Assay: Reverse phase HPLC was used to analyze the reaction mixtures. A 5 μm Beckman/Altex Ultrasphere-ODS (4.6×150 mm) column was employed using a ternary gradient pump system.

| Time (min) | Flow Rate (mL/Min) | Elution Gradient | | |
|---|---|---|---|---|
| | | % Water | % ACN | % MeOH |
| 0 | 1.5 | 90 | 10 | 0 |
| 12.0 | 1.5 | 63 | 30 | 8 |
| 12.1 | 1.5 | 60 | 20 | 20 |
| 15 | 1.5 | 60 | 20 | 20 |
| 35 | 1.5 | 10 | 45 | 45 |
| 40 | 1.5 | 10 | 45 | 45 |
| 41 | 1.5 | 90 | 10 | 0 |
| 50 | 1.5 | 90 | 10 | 0 |

EXAMPLE 1

A) This example illustrates a neat reaction of aniline and nitrobenzene under aerobic conditions at room temperature to generate 4-NDPA and p-nitrosodiphenylamine (p-NDPA) products. The reaction mixture was then hydrogenated directly to generate 4-ADPA.

A 500 mL three-necked round bottom flask was equipped with a magnetic stir bar. The reaction vessel was charged with 196 mL of aniline and nitrobenzene (4.3 mL, 42 mmole). To the stirred reaction mixture was added tetramethylammonium hydroxide dihydrate (17.7 grams, 140 mmoles) as a solid. The reaction was shown to have consumed nearly all the nitrobenzene after two hours, however, the reaction was allowed to stir for 18 hours. After this time >99% of the nitrobenzene was consumed. HPLC analysis of the reaction mixture indicated the following yields of products based on nitrobenzene: 4-NDPA (6.4 mmole, 1.37 g, 15%). p-NDPA (30.6 mmole, 6.1 g, 73%), 2-NDPA (0.3 mmole, 0.064 g, 0.7%), azobenzene (3.6 mmole, 0.65 g, 8.5%), phenazine (0.8 mmole, 0.14 g, 1.9%). phenazine-N-oxide (0.3 mmole, 0.05 g, 0.7%).

Water (16 ml) was added to the mixture and the entire reaction was then charged into a 300 cc autoclave for hydrogenation. A 1% Pt/carbon catalyst (0.5 grams dry weight) was added to the autoclave. The reaction mixture was heated to 80° C. under 150 psig of $H_2$. Hydrogen uptake was complete Within 30 minutes. HPLC analysis indicated that 35.9 mmole of 4-ADPA was produced which corresponds to a 97% yield based on moles of 4-NDPA and p-NDPA.

B) This is an example of the reaction of aniline and nitrobenzene at room temperature in dimethylsulfoxide under anaerobic conditions.

A 25 mL round bottom flask was charged with 4 mL of DMSO, aniline, (200 μL, 1.9 mmole) and tetramethylammonium hydroxide dihydrate (330 mg, 2.5 mmole) under argon. The reaction was allowed to proceed at room temperature for 4 hours. Conversion of nitrobenzene was 68%. HPLC analysis indicated the following yields based on nitrobenzene. 4-NDPA (30.5%), p-NDPA (33.6%), azobenzene (2.6%), azoxybenzene (trace).

C) This is an example of a neat reaction between aniline and nitrobenzene at room temperature under anaerobic conditions.

A 25 mL round-bottom flask was charged with aniline (1.8 mL) and nitrobenzene (0.02 mL, 0.19 mmole) in a controlled atmosphere glove box filled with argon. To this solution was added tetramethylammonium hydroxide dihydrate (330 mg, 2.5 mmole). All the nitrobenzene was consumed after several hours. HPLC analysis indicated the following yields based on nitrobenzene: 4-NDPA 10%. p-NDPA 76%, azobenzene 7%, and phenazine 5%.

D) This is an example of the reaction between aniline and nitrobenzene at room temperature in DMSO under aerobic conditions. This example also illustrates generation of 4-NDPA and p-NDPA from its salts utilizing water and acid.

The reaction mixture contained aniline (200 μL, 2.1mmole) and nitrobenzene (200 μL, 1.9 mmole) in 4 mL of DMSO. Tetramethylammonium hydroxide dihydrate (330 mg, 2.5 mmole) was added in one portion. The reaction was allowed to stir for 18 hours after which time 80% of the nitrobenzene had been consumed. The reaction was dumped into 200 mL of water which caused the immediate precipitation of 4-NDPA. The solution was cooled on ice for several hours and the product was filtered off and dried at 100° C. The filtrate was treated with glacial acetic acid until the pH was neutral which caused the precipitation of p-NDPA. The precipitate was filtered and dried at 100° C. Isolated yields based on nitrobenzene consumed: 4-NDPA (66%), p-NDPA (29%).

E) This is an example of the reaction of aniline and nitrobenzene in DMSO at 80° C. under aerobic conditions.

A 250 mL round-bottom flask was charged with aniline (0.05 mole, 4.6 g), nitrobenzene (0.05 mole, 6.1 g) and 75 mL of DMSO. Tetramethylammonium hydroxide dihydrate (0.2 mole, 25.44g) was added to the solution in one portion. The reaction mixture was heated to 80° C. in an oil bath and maintained at that temperature for 5 hours. The reaction was analyzed by HPLC. Yields based on nitrobenzene; 4-NDPA (35%), p-NDPA (51), azobenzene (3.1%).

F) This is an example of the reaction of aniline and nitrobenzene in DMF under aerobic conditions.

Aniline (200 μL, 2.1 mmole) and nitrobenzene (200 μL, 1.9 mmole) was dissolved in 5 mL of DMF. Tetramethylammonium hydroxide dihydrate (1.0 g, 7.8 mmole) was added to the reaction. The reaction was allowed to stir for 2 hours during which time 39% of the nitrobenzene was consumed. Yields based on nitrobenzene consumed: 4-NDPA 99%, p-NDPA trace.

EXAMPLE 2

This example illustrates that the reaction of the present invention can be conducted over a range of temperatures. Four identical reactions were prepared in the following manner and were run at 0°, 23°, 50° and 80° C. in the air. A 50 mL round-bottom flask was charged with 49 mL of aniline and nitrobenzene (1.0 mL, 9.5 mmole). Tetramethylammonium hydroxide dihydrate (4.40 g, 34.6 mmole) was added and the reaction was allowed to proceed for 5 hours. Product yields were determined by HPLC analysis and are based on moles nitrobenzene consumed. Selectivity is the ratio of the moles of product generated and the moles of nitrobenzene consumed. Yield is conversion times selectivity.

TABLE 1

| Temp. °C. | Nitrobenzene Conversion | Products | % Selectivity | % Yield |
|---|---|---|---|---|
| 0 | 52% | p-NDPA | 34 | 18 |
| | | 4-NDPA | 18 | 9.3 |
| | | 2-NDPA | 2.2 | 1.0 |
| | | phenazine | 0.6 | 0.3 |
| 23 | 73% | p-NDPA | 71 | 51 |

TABLE 1-continued

| Temp. °C. | Nitrobenzene Conversion | Products | % Selectivity | % Yield |
|---|---|---|---|---|
| | | 4-NDPA | 12 | 8.5 |
| | | azobenzene | 17 | 12 |
| | | phenazine | | trace |
| | | phenazine-N-oxide | | trace |
| 50 | 98% | p-NDPA | 88 | 86 |
| | | 4-NDPA | 7.8 | 7.6 |
| | | 2-NDPA | 1.7 | 1.6 |
| | | azobenzene* | 22 | 21 |
| 80 | 100% | p-NDPA | 89 | 89 |
| | | 4-NDPA | 7 | 7 |
| | | 2-NDPA | 2 | 2 |
| | | azobenzene* | 55 | 55 |

*The majority of azobenzene is produced presumably through oxidative coupling of aniline. See D. T. Sawyer paper.

EXAMPLE 3

This example illustrates that control of the amount of protic material present in the reaction is important. Four identical reactions were run except the amount of water added to the mixture was varied to include 0, 10, 50, and 100µL. Thus aniline (2 mL) and nitrobenzene (2 mL) were charged into a 25 mL round-bottom flask and various amounts of water were added. Tetramethylammonium hydroxide dihydrate (330 mg, 2.5 mmole) was added in one portion. The reactions were allowed to run in the air at room temperature and were sampled after 16 hours. An identical set of reactions was also run where methanol was added instead of water.

TABLE 2

| Volume (µL) | % | Ratio mmole 4-NDPA + p-NDPA/ 2-NDPA + Phenazine | Yield (mmole) 4-NDPA + p-NDPA |
|---|---|---|---|
| Water Added | Water* | | |
| 0 | 2.2 | 6.2 | 0.83 |
| 10 | 2.45 | 8.5 | 0.68 |
| 50 | 3.45 | 11.5 | 0.18 |
| 100 | 4.7 | 5.0 | 0.05 |
| Methanol Added | Methanol* | | |
| 10 | 0.25 | 8.8 | 0.67 |
| 50 | 1.25 | 16 | 0.57 |
| 100 | 2.5 | 35 | 0.42 |

*The % water and methanol is by volume. In the case when no water was added the water present in the reaction was introduced from the tetramethylammonium hydroxide dihydrate.

EXAMPLE 4

This example illustrates that various solvents can be utilized in the practice of the method of this invention to produce 4-NDPA and/or p-NDPA products. The reactions set forth in Table 3 were conducted as in as indicated, except that the solvent of was changed to that indicated in the table.

TABLE 3

| Solvent | Reaction Conditions |
|---|---|
| 1-methyl-2-pyrrolidinone | 1D |
| DMSO/THF | 1B |
| pyridine | 1D |

EXAMPLE 5

This example illustrates various bases which can be utilized in the method of the present invention to produce 4-NDPA and/or p-NDPA products. The reactions set forth in Table 4 were conducted as in Example 1 as indicated except that the base of Example 1 was changed to that indicated in the table.

TABLE 4

| Base | Reaction Conditions |
|---|---|
| Na metal | 1D |
| NaH | 1D |
| NaOH | 1D |
| KOH | 1D |
| Potassium t-butoxide | 1D |
| Lithium bis(trimethylsilyl)amide | 1B, 1D |
| NaOH/K$_2$CO$_3$ | 1D, 1F |

EXAMPLE 6

This example illustrates the unexpected increase in selectivity and nitrobenzene conversion utilizing the method of the present invention as compared to the method disclosed in Ayyangar et al.

The reaction of acetanilide, nitrobenzene, NaOH, and K$_2$CO$_3$ in DMSO was run according to the procedure described by Ayyangar et al. Tetrahedron Letters, Vol. 31, No. 22, pp 3217-3220 (1990). Analysis of this reaction by HPLC indicated 37% of the nitrobenzene was converted and the following yields based on nitrobenzene, were achieved. 4-NDPA (6%), p-NDPA (4.5%), azobenzene (0.7%).

In comparison, when the reaction is conducted according to the teachings of the present invention, the conversions of nitrobenzene and selectivities to the desired products are greatly increased. For example, conducting the reaction as described in Example 1D, aniline (0.05 mole), nitrobenzene (0.05 mole) and tetramethylammonium hydroxide dihydrate (0.2 mole) were mixed in 75 mL of DMSO. The reaction was stirred at room temperature for 5 hours after which time the reaction was analyzed by HPLC chromatography giving the following results. Nitrobenzene conversion was (85%). Yield based on nitrobenzene: 4-NDPA (18%), p-NDPA (51%) azobenzene (3%).

The reaction of acetanilide and nitrobenzene was also run at room temperature. Thus, acetanilide (0.05 mole), nitrobenzene (0.05 mole), NaOH (0.2 mole) and K$_2$CO$_3$ were dissolved in 75 mL of DMSO. The reaction was stirred for 5 hours at room temperature (23° C.). Analysis of the reaction showed no conversion of nitrobenzene and no products detected.

EXAMPLE 7

This example illustrates how the ratio of p-NDPA/4-NDPA can be controlled by the ratio of aniline/nitrobenzene.

Aniline and nitrobenzene were reacted at various ratios, while the total reaction volume and the amount of tetramethylammonium hydroxide dihydrate were held constant. Thus, in a typical reaction illustrating an aniline/nitrobenzene volume ratio of 1, aniline (2 mL) and nitrobenzene (2 mL) were charged into a 25 mL round-bottom flask. Tetramethylammonium hydroxide dihydrate (330 mg, 2.5 mmole) was added and the reaction was allowed to proceed at room temperature in air for 14 hours. The reactions were then analyzed by HPLC.

TABLE 5

| Volume Ratio Aniline/Nitrobenzene | Ratio p-NDPA/4-NDPA |
|---|---|
| 0.33 | 0.1 |

TABLE 5-continued

| Volume Ratio Aniline/Nitrobenzene | Ratio p-NDPA/4-NDPA |
|---|---|
| 1 | 0.1 |
| 10 | 4 |
| 50 | 6 |

EXAMPLE 8

This example illustrates the effect that the amount of protic material present in or added to the reaction has on the extent of conversion and yields of 4-NDPA and p-NDPA.

The amount of water added to a reaction of aniline, nitrobenzene and tetramethylammonium hydroxide dihydrate in DMSO was varied from zero to 500 μL (0, 50, 150, 300, 500 μL) while keeping the total reaction volume constant. Thus, a typical reaction contained aniline, (200 μL, 2.1 mmole), nitrobenzene (200 μL, 1.9 mmole), tetramethylammonium hydroxide dihydrate (330 mg, 2.5 mmole) and water (50 μL) in 3.55 mL of anhydrous DMSO. The reaction was allowed to react aerobically at room temperature 24 hours after which time it was sampled and subjected to HPLC analysis.

TABLE 6

| Volume (μL) Water Added | % Water | % Conversion Nitrobenzene | Yield (mmole) 4-NDPA + p-NDPA |
|---|---|---|---|
| 0 | 2.3 | 89 | 150 |
| 50 | 3.5 | 73 | 99 |
| 150 | 6 | 63 | 62 |
| 300 | 9.75 | 12 | 0.23 |
| 500 | 14.7 | 3 | 0.05 |

EXAMPLE 9

This example illustrates the effect that increasing the amount of base has on yields of 4-NDPA and p-NDPA under conditions where the amount of protic material added to the reaction is kept constant.

Three identical reactions were run except that the amount of tetramethylammonium hydroxide dihydrate was varied in each. In a typical reaction, aniline (2 mL), nitrobenzene (2 mL), water (100 μL) and tetramethylammonium hydroxide dihydrate (330 mg, 2.5 mmole) were mixed and allowed to react for 24 hours at room temperature in the air. In those cases where the solution showed large amounts of precipitates, an addition 10 mL of aniline was added to solubilize the reaction before sampling. All of these reactions were analyzed by HPLC.

TABLE 7

| Volume Water Added | % Water | Grams Base | mMoles Base | Yield (mmole) 4-NDPA + p-NDPA |
|---|---|---|---|---|
| 100 | 4.7 | 0.330 | 2.5 | 0.05 |
| 100 | 4.7 | 0.660 | 5.0 | 0.15 |
| 100 | 4.7 | 1.65 | 12.5 | 1.24 |

EXAMPLE 10

This example illustrates the reaction of aniline, nitrobenzene and tetramethylammonium hydroxide dihydrate under anaerobic conditions at 50° C.

A 500 mL four-necked round-bottom flask equipped with a mechanical stirrer, addition funnel, thermometer, and nitrogen inlet was charged with 90 mL of aniline. The aniline was purged with nitrogen and tetramethylammonium hydroxide dihydrate (54 g, 0.42 mole) was added in one portion. The reaction mixture was heated to 50° C. under a nitrogen blanket with stirring. Once the temperature in the reaction vessel reached 50° C., nitrobenzene (10 mL, 95 mmole) was added dropwise to the vigorously stirred mixture of aniline and base. The nitrobenzene was added at a rate such that the addition was complete within 30 minutes. The temperature of the reaction increased to 65° C. during the nitrobenzene addition. The reaction was allowed to stir for an additional 90 minutes after which time it was analyzed by HPLC. Nitrobenzene conversion = 100%. Yields based on nitrobenzene: p-NDPA (88.5%), 4-NDPA (4.3%), phenazine (3.6%), azobenzene (3.6%).

EXAMPLE 11

This example illustrates that tetramethylammonium ion salt of 4-NDPA and p-NDPA can be produced in the method of the present invention.

Aniline (3.0 mL) was stirred with tetramethylammonium hydroxide dihydrate (330 mg, 2.5 mmole) in a controlled atmosphere dry box under argon. The aniline base mixture was filtered such that the aniline was delivered directly to 1 mL of nitrobenzene. Upon addition of the aniline-base solution, the reaction immediately turned red and a precipitate began to form. The mixture was allowed to stir for 5 minutes after which time the reaction was filtered. The red precipitate was washed with several volumes of dry ether and allowed to dry. A portion of the solid was analyzed by $^1$H-NMR spectroscopy: (DMSO) δ 3.1(s), 6.1 (d, 1), 6.5 (t, 1), 6.6 (d,1), 6.76 (d, 1), 6.8 (t, 1), 7.04 (t, 1) 7.5 (d,1). A drop of acetic acid-$d_4$ was added to the NMR tube which caused an immediate color change from red to yellow and the sample was re-subjected to $^1$H-NMR spectroscopy. The resulting spectrum was identical to authentic 4-NDPA. A portion of the red solid was dissolved in wet acetonitrile and subjected to HPLC analysis which indicated that 4-NDPA was the major component.

EXAMPLE 12

This example illustrates the conversion of 4-ADPA to N-(1,3-dimethylbutyl)-N'-phenyl-p-phenylenediamine, a useful antiozonant for the protection of rubber products.

52 grams of 4-ADPA, prepared by the reaction of aniline and nitrobenzene (by the procedure of Example 1D), 100 grams methylisobutylketone (MIBK) and 0.3 grams of 3% platinum on carbon catalyst were charged into a one liter Parr autoclave. After purging with hydrogen, the reaction mixture was heated to 170°-175° C. and 800 psig hydrogen applied. The mixture was reacted for 95 minutes and a sample withdrawn. GC analysis indicated 0.4% unreacted 4-ADPA present. The reaction mixture was cooled and filtered to remove catalyst and stripped to remove water and excess MIBK. The product, 71 grams, on cooling crystallized to a purplish solid. Assay by GC internal standard method indicated 95.9% purity.

Similar reactions were conducted with similar results using methylisoamylketone and acetone.

The preceding examples can be repeated with similar success by substituting the generically or specifically described solvents, bases and the like and/or operating conditions, such as other temperatures and pressures, of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of producing one or more 4-ADPA intermediates comprising the steps of:
   a) bringing aniline and nitrobenzene into reactive contact in a suitable solvent system; and
   b) reacting the aniline and nitrobenzene in a confined zone at a suitable temperature, and in the presence of a suitable base and a controlled amount of protic material to produce one or more 4-ADPA intermediates.

2. Method of claim 1 wherein said suitable solvent system includes a solvent selected from aniline, nitrobenzene, dimethylsulfoxide, dimethylformamide, pyridine and mixtures thereof.

3. Method of claim 2 wherein said solvent is selected from aniline, dimethylsulfoxide, and dimethylformamide.

4. Method of claim 2 wherein said solvent is aniline.

5. Method of claim 2 wherein said solvent is nitrobenzene.

6. Method of claim 2 wherein said solvent is dimethylsulfoxide.

7. Method of claim 2 wherein said solvent is dimethylformamide.

8. Method of claim 2 wherein said solvent is N-methylpyrolidone.

9. Method of claim 2 wherein said solvent is pyridine.

10. Method of claim 2 wherein said suitable solvent system includes a protic solvent.

11. Method of claim 10 wherein said protic solvent is selected from methanol, water and mixtures thereof.

12. Method of claim 1 wherein said solvent system includes aniline and up to about 4 v/v % water based on the total volume of the reaction mixture.

13. Method of claim 1 wherein said solvent system includes dimethylsulfoxide and up to about 8 v/v % water based on the total volume of the reaction mixture.

14. Method of claim 1 wherein said solvent system includes aniline and up to about 3 v/v % methanol based on the total volume of the reaction mixture.

15. Method of claim 1 wherein said suitable temperature is from about −10° C. to about 150° C.

16. Method of claim 1 wherein said suitable base is selected from organic and inorganic bases.

17. The method of claim 16 wherein said organic and inorganic bases include alkali metals, alkali metal hydrides, alkali metal hydroxides, alkali metal alkoxides, phase transfer catalysts in conjunction with a base source, aminos and mixtures thereof.

18. The method of claim 1 wherein said base is an alkali metal.

19. The method of claim 1 wherein said base is an alkali metal hydride.

20. The method of claim 1 wherein said base is an alkali metal hydroxide.

21. The method of claim 1 wherein said base is a phase transfer catalyst in conjunction with a base source.

22. The method of claim 1 wherein said base is selected from an aryl, alkyl, and aryl/alkyl ammonium salt in conjunction with a base source.

23. The method of claim 1 wherein said base is a crown ether.

24. The method of claim 1 wherein said base is an amine.

25. The method of claim 1 wherein said base is combined with aniline to form a mixture, which mixture is then brought into reactive contact with nitrobenzene.

26. The method of claim 1 wherein said aniline and nitrobenzene are combined to form a mixture to which the base is added.

27. The method of claim 1 wherein said solvent is aniline and said base is a tetraalkylammonium hydroxide.

28. The method of claim 1 wherein said aniline and nitrobenzene are reacted under aerobic conditions.

29. The method of claim 1 wherein said aniline and nitrobenzene are reacted under anaerobic conditions.

30. A method of producing 4-aminodiphenylamine (4-ADPA) comprising the steps of:
   a) bringing aniline and nitrobenzene into reactive contact in a suitable solvent system;
   b) reacting the aniline and nitrobenzene in a confined zone at a suitable temperature, and in the presence of a suitable base and controlled amount of protic material to produce one or more 4-ADPA intermediates; and
   c) reducing the 4-ADPA intermediates under conditions which produce 4-ADPA.

31. Method of claim 30 wherein said suitable solvent system includes a solvent selected from aniline, nitrobenzene, dimethylsulfoxide, dimethylformamide, N-methylpyrolidone, pyridine and mixtures thereof.

32. Method of claim 31 wherein said solvent is selected from aniline, dimethylsulfoxide, dimethylformamide, and mixtures thereof.

33. Method of claim 31 wherein said solvent is aniline.

34. Method of claim 31 wherein said solvent is nitrobenzene.

35. Method of claim 31 wherein said solvent is dimethylsulfoxide.

36. Method of claim 31 wherein said solvent is dimethylformamide.

37. Method of claim 31 wherein said solvent is N-methylpyrolidone.

38. Method of claim 31 wherein said solvent is pyridine.

39. Method of claim 31 wherein said suitable solvent system includes a protic solvent.

40. Method of claim 39 wherein said protic solvent is selected from methanol, water and mixtures thereof.

41. Method of claim 30 wherein said solvent system includes aniline and up to about 4 v/v % water based on the total volume of the reaction mixture.

42. Method of claim 30 wherein said solvent system includes dimethylsulfoxide and up to about 8 v/v % water based on the volume of the reaction mixture.

43. Method of claim 30 wherein said solvent system includes aniline and up to about 3 v/v % methanol based on the volume of the reaction mixture.

44. Method of claim 30 wherein said suitable temperature is from about −10° C. to about 150° C.

45. Method of claim 30 wherein said suitable base is selected from organic and inorganic bases.

46. The method of claim 45 wherein said organic and inorganic bases include alkali metals, alkali metal hydrides, alkali metal hydroxides, phase transfer catalysts in conjunction with a base source, and mixtures thereof.

47. The method of claim 30 wherein said base is an alkali metal.

48. The method of claim 30 wherein said base is an alkali metal hydride.

49. The method of claim 30 wherein said base is an alkali metal hydroxide.

50. The method of claim 30 wherein said base is a phase transfer catalyst in conjunction with a base source.

51. The method of claim 30 wherein said base is selected from an aryl, alkyl and aryl/alkyl ammonium salt in conjunction with a base source.

52. The method of claim 30 wherein said base is a crown ether in conjunction with a base source.

53. The method of claim 30 wherein said base is an amine.

54. The method of claim 30 wherein said base is combined with aniline to form a mixture, which mixture is then brought into reactive contact with nitrobenzene.

55. The method of claim 30 wherein said aniline and nitrobenzene are combined to form a mixture to which the base is added.

56. The method of claim 30 wherein said solvent is aniline and said base is a tetraalkylammonium hydroxide.

57. The method of claim 30 wherein said aniline and nitrobenzene are reacted under aerobic conditions.

58. The method of claim 30 wherein said aniline and nitrobenzene are reacted under anaerobic conditions.

59. A method of claim 30 wherein said 4-ADPA intermediates are reduced utilizing hydrogen in the presence of a suitable catalyst.

60. A method of claim 59 wherein said catalyst is platinum on carbon.

61. A method of producing alkylated p-phenylenediamines comprising the steps of:
   a) bringing aniline and nitrobenzene into reactive contact in a suitable solvent system;
   b) reacting the aniline and nitrobenzene in a confined zone at a suitable temperature, and in the presence of a suitable base and controlled amount of protic material to produce one or more 4-ADPA intermediates.
   c) reducing the 4-ADPA intermediates to produce 4-ADPA; and
   d) reductively alkylating the 4-ADPA of Step c).

62. Method of claim 61 wherein said suitable solvent system includes a solvent selected from aniline, nitrobenzene, dimethylsulfoxide, dimethylformamide, pyridine and mixtures thereof.

63. Method of claim 62 wherein said solvent is selected from aniline, dimethylsulfoxide, dimethylformamide, and mixtures thereof.

64. Method of claim 62 wherein said solvent is aniline.

65. Method of claim 62 wherein said solvent is nitrobenzene.

66. Method of claim 62 wherein said solvent is dimethylsulfoxide.

67. Method of claim 62 wherein said solvent is dimethylformamide.

68. Method of claim 62 wherein said solvent is N-methylpyrolidone.

69. Method of claim 62 wherein said solvent is pyridine.

70. Method of claim 62 wherein said suitable solvent system includes a protic solvent.

71. Method of claim 70 wherein said protic solvent is selected from methanol, water and mixtures thereof.

72. Method of claim 62 wherein said solvent system includes aniline and up to about 4 v/v % water based on the volume of the reaction mixture.

73. Method of claim 62 wherein said solvent system includes dimethylsulfoxide and up to about 8 v/v % water based on the volume of the reaction mixture.

74. Method of claim 62 wherein said solvent system includes aniline and up to about 3 v/v % methanol based on the volume of the reaction mixture.

75. Method of claim 62 wherein said suitable temperature is from about −10° C. to about 150° C.

76. Method of claim 62 wherein said suitable base is selected from organic and inorganic bases.

77. The method of claim 76 wherein said organic and inorganic bases include alkali metals, alkali metal hydrides, alkali metal hydroxides, alkali metal alkoxides, phase transfer catalysts in conjunction with a base source, amines and mixtures thereof.

78. The method of claim 62 wherein said base is an alkali metal.

79. The method of claim 62 wherein said base is an alkali metal hydride.

80. The method of claim 62 wherein said base is an alkali metal hydroxide.

81. The method of claim 62 wherein said base is a phase transfer catalyst in conjunction with a base source.

82. The method of claim 62 wherein said base is selected from an aryl, alkyl, and aryl/alkyl ammonium salt in conjunction with a base source.

83. The method of claim 62 wherein said base is a crown ether.

84. The method of claim 62 wherein said base is an amine.

85. The method of claim 62 wherein said base is combined with aniline to form a mixture, which mixture is then brought into reactive contact with nitrobenzene.

86. The method of claim 62 wherein said aniline and nitrobenzene are combined to form a mixture to which the base is added.

87. The method of claim 62 wherein said solvent is aniline and said base is a tetraalkylammonium hydroxide.

88. The method of claim 62 wherein said aniline and nitrobenzene are reacted under aerobic conditions.

89. The method of claim 62 wherein said aniline and nitrobenzene are reacted under anaerobic conditions.

90. The method of claim 61 Wherein said 4-ADPA is reductively alkylated utilizing a ketone selected from the group consisting of acetone, methylisobutylketone, methylisoamylketone, and 2-octanone.

91. Method of claim 90 wherein said ketone is acetone.

92. Method of claim 90 wherein said ketone is methylisobutylketone.

93. Method of claim 90 wherein said ketone is methylisoamylketone.

94. Method of claim 90 wherein said ketone is 2-octanone.

* * * * *